United States Patent [19]
El Gazayerli

[11] Patent Number: 6,159,146
[45] Date of Patent: Dec. 12, 2000

[54] METHOD AND APPARATUS FOR MINIMALLY-INVASIVE FUNDOPLICATION

[76] Inventor: Mohamed Mounir El Gazayerli, 476 Steeple Chase Ct., Bloomfield Hills, Mich. 48304

[21] Appl. No.: 09/289,706

[22] Filed: Apr. 12, 1999

Related U.S. Application Data

[60] Provisional application No. 60/124,080, Mar. 12, 1999.

[51] Int. Cl.$^7$ .......................... A61B 1/00; A61B 17/062
[52] U.S. Cl. ............................................ 600/106; 600/104
[58] Field of Search ............................. 600/106, 107, 600/141, 142, 104; 606/106

[56] References Cited

U.S. PATENT DOCUMENTS

| | | | |
|---|---|---|---|
| 4,653,476 | 3/1987 | Bonnet | 600/106 |
| 4,700,694 | 10/1987 | Shishido | 600/106 |
| 4,841,949 | 6/1989 | Shimizu et al. | 600/107 |
| 5,088,979 | 2/1992 | Filipi et al. | |
| 5,311,858 | 5/1994 | Adair | 600/106 |
| 5,336,227 | 8/1994 | Nakao et al. | 600/106 |
| 5,373,840 | 12/1994 | Knighton | 600/106 |
| 5,382,231 | 1/1995 | Shlain | |
| 5,417,203 | 5/1995 | Tovey et al. | 600/106 |
| 5,445,154 | 8/1995 | Larson et al. | |
| 5,479,930 | 1/1996 | Gruner et al. | |
| 5,558,665 | 9/1996 | Kieturakis | 600/141 |
| 5,571,116 | 11/1996 | Bolanos et al. | |
| 5,676,674 | 10/1997 | Bolanos et al. | |
| 5,787,897 | 8/1998 | Kieturakis | 600/141 |
| 5,833,616 | 11/1998 | Gruner et al. | |
| 5,842,993 | 12/1998 | Eichelberger et al. | |
| 5,887,594 | 3/1999 | LoCicero, III | |

*Primary Examiner*—Paul J. Hirsch
*Attorney, Agent, or Firm*—Reising, Ethington, Barnes, Kisselle, Learman & McCulloch, P.C.

[57] ABSTRACT

A method and apparatus for performing a non-invasive fundoplication. The method involves: inserting a device through a patient's mouth and esophagus to a location near the gastro-esophageal junction; viewing portions of the stomach and esophagus; engaging the inside anterior wall of the fundus with the device; moving the fundus to a location adjacent the esophagus with the device; and securing the fundus to the side of the esophagus with the device. The device includes a flexible conduit (12) and a gastroscope (14) extending through the conduit. A stapler (16) also extends through the conduit. The stapler (16) sits at the bottom of the conduit in the esophagus just above the gastro-esophageal junction. A gripper (22) extends through and beyond the conduit. The gripper (22) has a gripping head (24) capable of gripping the fundus, and a linkage (28) that can move the gripping head and the gripped part of the fundus to the remote side of the esophagus where the stapler (16) will staple the fundus to the esophagus, using the gripper as an anvil.

16 Claims, 12 Drawing Sheets

METHOD AND APPARATUS FOR MINIMALLY-INVASIVE FUNDOPLICATION

CROSS REFERENCE TO RELATED APPLICATION

This application claims the benefit of the filing date of U.S. Provisional Application No. 60/124,080, filed Mar. 12, 1999 by the Applicant.

TECHNICAL FIELD

The subject invention relates to a method and apparatus for performing non-invasive, or minimally invasive, surgical techniques; and more particularly to techniques for gastro-esophageal surgery.

BACKGROUND OF THE INVENTION

Hiatal hernia and reflux disease are prevalent in the USA and other countries. It is estimated that 40% of the adult population suffer heartburn, and that 10 to 20% of these have complications and are candidates for surgical correction of their reflux. In addition to that, a large number of infants are born with reflux disease that can stunt their growth. Respiratory complications in adults and children can result in asthmatic bronchitis and recurrent infections of the lungs. Fifty percent of asthmatics also have reflux disease, and their symptoms and suffering has been shown to markedly decrease after surgery to correct the reflux.

Surgical methods to adequately control reflux have existed since the 1950's and have involved thoracic or abdominal incisions. One example is taught in the paper, "Traitement du Reflux Par la Technique Dite de Heller-Nissen Modifee," Dor et al, Presse Medicale, 75(50): 2563–5, Nov. 25, 1967. The Dor technique for fundoplication involves gripping the anterior portion of the fundus and attaching it to the lower part of the esophagus. This technique and its variants are quite effective in controlling reflux. But they all involve invasive surgery (i.e surgery involving incisions) and its consequences.

Since the early 1990's laparoscopic adaptations of these procedures have reduced the morbidity of the procedures by using 4 to 6 small incisions through which trocars are inserted into the abdomen and by operating under videoscopic visualization. This involves a general anesthetic and a short hospital admission.

Very recently, a few people have devised non-invasive techniques for controlling reflux. U.S. Pat. No. 5,887,594 to LoCicero shows one technique that attaches the esophagus and a portion of the stomach that is immediately adjacent the esophagus. U.S. Pat. Nos. 5,676,674 and 5,571,116 to Bolanos et al. shows another technique for attaching the esophagus and a portion of the stomach that is immediately adjacent the esophagus. Both are different from the present invention because they do not perform a fundoplication. They attempt to accentuate the gastro-esophageal junction by stapling or inserting a stud.

SUMMARY OF THE INVENTION AND ADVANTAGES

An inventive method for controlling reflux includes the basic steps of: inserting a device through the mouth and esophagus of a patient to a predetermined location near the gastro-esophageal junction; viewing portions of the stomach and esophagus with the device; engaging a portion of the inside anterior wall of the stomach with the device at a location between the greater curvature and the gastro-esophageal junction; moving the portion of the inside wall with the device to a location adjacent the esophagus; and securing the inside portion to the esophagus with the device at a location remote from the fundus.

A corresponding inventive apparatus includes a flexible elongated conduit that extends from a proximal end to a spaced-apart distal end. A viewing device extends through the conduit. A fastening device also extends through the conduit. The fastening device has an actuator at the proximal end and a fastener applicator at the distal end. An elongated gripper mechanism extends through and beyond the conduit. The gripper mechanism includes a gripping head disposed at a distal end of the gripper mechanism capable of moving between a neutral configuration and a gripping configuration in which the gripping head grips desired body tissue such as the fundus. The gripper mechanism also includes a manipulable control at a proximal end of the gripper for controlling the position and configuration of the gripping head. An elongated linkage—also part of the gripper mechanism—extends along an axis interconnecting the control and the gripping head. The linkage is adapted to move the gripping head in response to manipulation of the control.

The present method and device have been developed to eliminate any trocar insertion into the abdomen—or at least reduce those to one specialized trocar to be used, if necessary while a physician is learning the new technique. When no trocars are used the procedure can be performed under sedation and the patient can be discharged shortly after the intervention.

Moreover, this non-invasive technique adapts a well-known and effective method.—the Dor method. This Dor method is well-established and trusted as being effective in controlling reflux, and especially difficult and repeat cases. But this new method avoids the consequences of the invasive aspect of the Dor method.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Referring to the Figures, like numerals indicate like or corresponding parts throughout the several views. This description first discusses the preferred apparatus and certain variants; and then discusses the inventive method, which may be performed with any suitable apparatus.

APPARATUS

Figure 1:
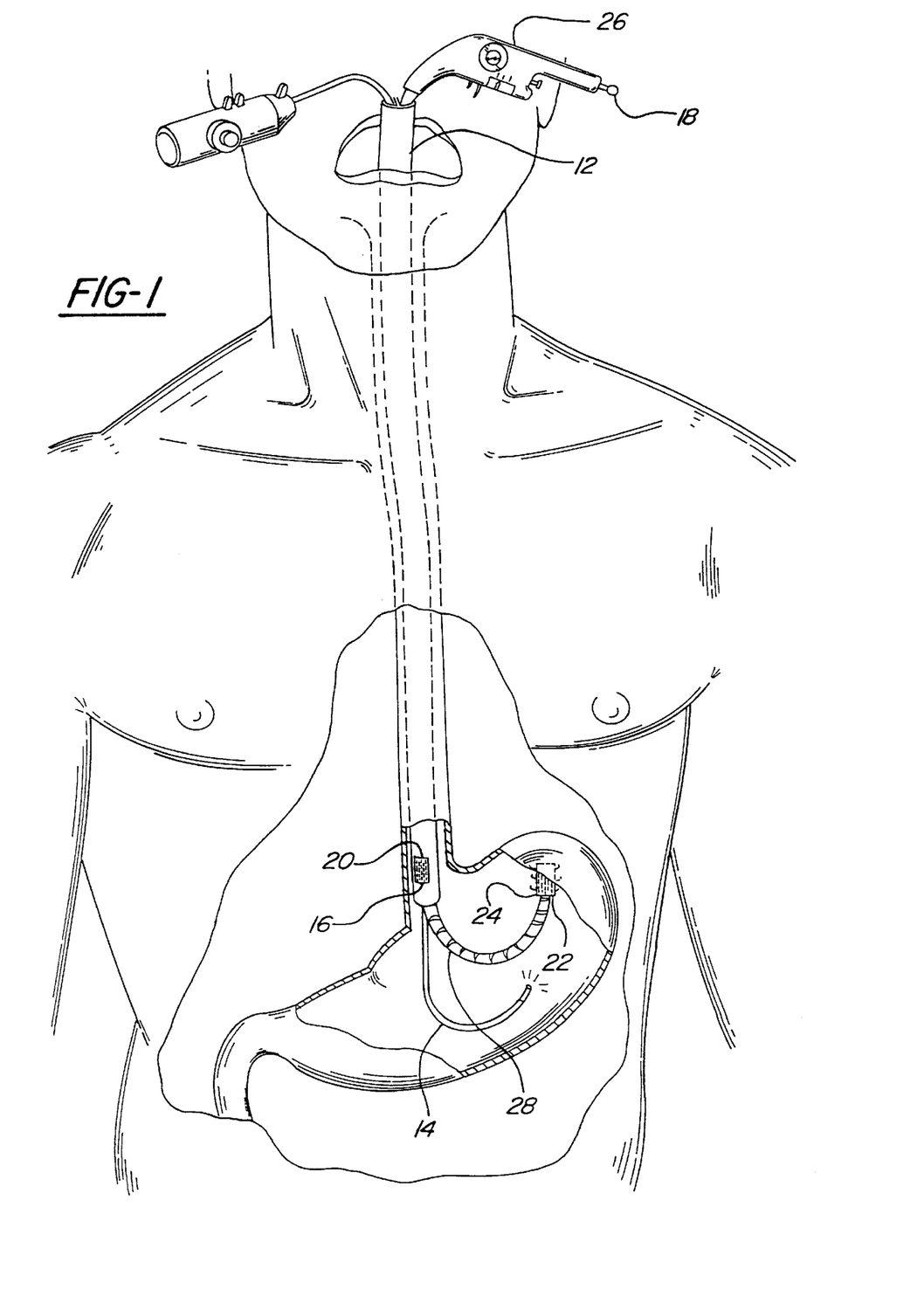
FIG. 1 is a front perspective view showing one embodiment of the apparatus in operation with the gripping head gripping a portion of the fundus.

FIG. 1 shows the basic elements of the apparatus. A flexible elongated conduit 12 extends from a proximal end (near the patient's mouth) to a spaced-apart distal end. A viewing device 14 extends through the conduit 12. A fastening device 16 also extends through the conduit. The fastening device 16 has an actuator 18 at the proximal end and a fastener applicator 20 at the distal end. An elongated gripper mechanism 22 extends through and beyond the conduit 12. The gripper mechanism 22 includes a gripping head 24 disposed at a distal end of the gripper mechanism capable of moving between a starting or neutral (i.e. non-gripping) configuration and a gripping configuration in which the gripping head grips desired body tissue. The gripper mechanism 22 also includes a manipulable control 26 at a proximal end of the gripper mechanism for controlling the position and configuration of the gripping head 24. (See FIG. 4A). An elongated linkage 28—also part of the gripper mechanism 22—extends along an axis interconnecting the control 26 and the gripping head 24. The linkage 28 is adapted to move the gripping head 24 in response to manipulation of the control 26.

The conduit 12 is a flexible tube approximately 60 centimeters in length. It may be made of any appropriate material. The conduit 12 may have three or more channels or sub-conduits extending through it to support and guide the various elements of the apparatus.

The elongated, snake-like linkage 28 may assume one of several embodiments. According to a presently preferred embodiment, shown in FIGS. 4A–4C, the linkage 28 includes a plurality of elements 30 disposed in series along the axis (the axis is approximated by the item indicated at 34). Each element includes at least two alignment surfaces 32 extending across the axis and having a predetermined orientation with respect to the axis. The linkage 28 further includes an elongated draw line or core element 34 extending between the control and the gripper mechanism and through the elements 30. The draw line 34 may be a cable, a wire, a tube, a pair of cables, a cable doubled over itself or any other suitable motion transmitting core element. The draw line 34 is moveable between a slack state and a taut state wherein the elements 30 abut at the alignment surfaces 32 so that the linkage 28 assumes a predetermined configuration with the appropriate part of the gripping head 24 disposed adjacent the fastener applicator 20.

There are various other possible linkages that could serve to guide the gripping head 24. Examples are shown in U.S. Pat. Nos. 5,842,993; 5,833,616; 5,445,154; and 5,479,930. The teachings of these references are incorporated herein by reference. Similarly, persons of skill in the art know of other linkages, including linkages used to guide the heads of gastroscopes and other internal viewing devices.

Figure 3:
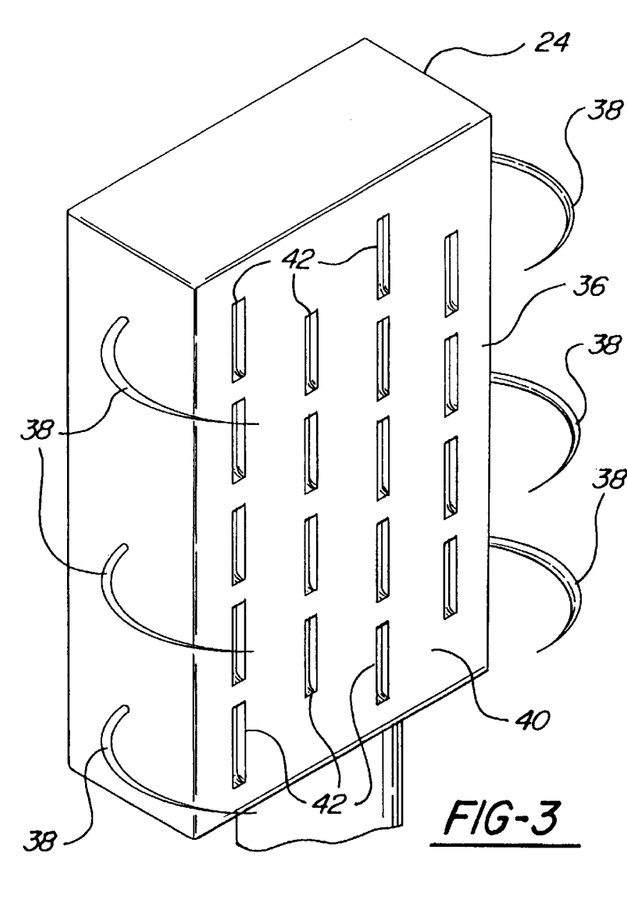
FIG. 3 is a perspective view of the gripping head.
Figure 3A:
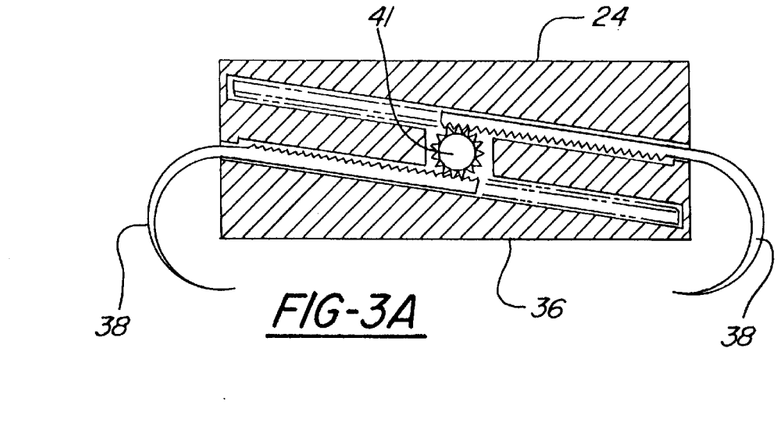
FIG. 3A is a perspective view of the gripping head partially cut away to show one embodiment of the gripping fingers.
Figure 3B:
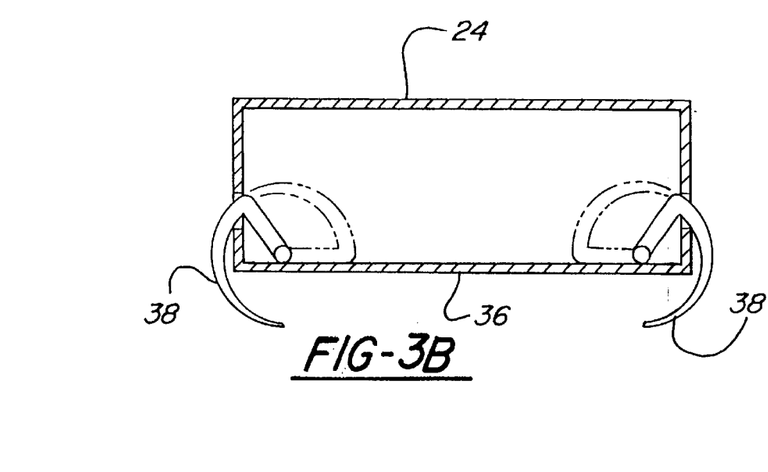
FIG. 3B is a perspective view of the gripping head partially cut away to show a second embodiment of the gripping fingers.

The gripping head 24 includes a block having a gripping face 36 and a plurality of gripping fingers 38 pivotally attached to the block for movement between a retracted position behind the gripping face 36 and an extended position where the gripping fingers 38 extend beyond the gripping face 36 to grip desired tissue. Ideally, the gripping fingers 38 grip by making fine penetrations in the gastric wall without tearing. FIGS. 3A and 3B show different embodiments of the gripping fingers 38 and associated hardware. According to FIG. 3A, for example, the gripping fingers 38 are made of spring steel or the like so that they can retract into the gripping head 24 as shown, or extend out of the gripping head and bias into a natural curved configuration. A finger-deploying core element 37, operated by knob 39, can rotate gear 41 to deploy the fingers 38 into the extended position. FIG. 3B shows an embodiment where the fingers 38 simply rotate into deployment in response to some rotating force. Both embodiments include arched, needle-like gripping fingers 38 that can selectively extend past the gripping face 36 to penetrate the gastric wall each at a single point in the mucosa. The exact number and location of the gripping fingers 38—or hooks—may vary.

The gripping face 36 includes an anvil surface 40 defining a plurality of shallow cavities 42 for shaping fasteners. These cavities 42 are much like the cavities on a common stapler. Indeed, the presently preferred fastener is a stapler of the type commonly used in surgical techniques. The anvil surface 40 includes approximately four columns each having multiple cavities 42 as shown in FIG. 3, where the columns are offset from one another.

The apparatus further includes a plurality of positioning cables 44 extending along the linkage 28 for controlling movement of the gripping head 24. This feature is common in ultrasound and gastroscope assemblies as shown in U.S. Pat. No. 5,842,993 to Eichelberger et al. The teachings of this patent are incorporated herein by reference. In any event, cable controls of this type are well-known to persons of skill in the surgical instrument art. Many different embodiments are possible.

The apparatus further includes a rotating assembly 46 associated with the gripping head 24 for rotating the gripping head about the axis of the linkage 28. According to one embodiment, the rotating assembly 46 includes a motion transmitting rotation core element extending along the linkage 28 between the control 26 and the gripping head 24. The core element is twisted at the proximal or control end, and the core element transmits this twisting movement to the gripping head 24, which is free to rotate axially with respect to the elements 30 in the linkage 28. The core element may be the same item as the draw line 34. The rotating assembly 46 may assume other embodiments and may include other elements. Many possibilities are known to persons of skill in the art for effecting a rotating motion in the gripping head 24.

Figures 4A, 4B:
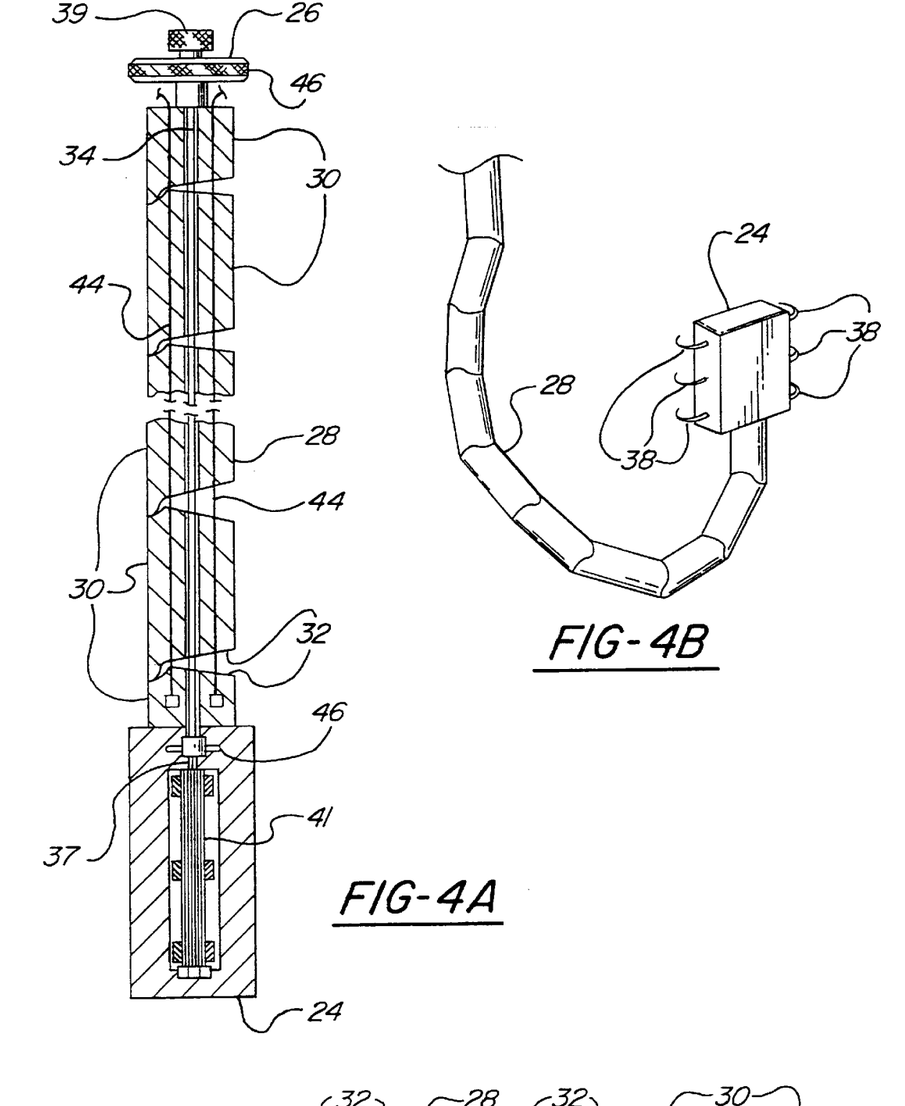
FIG. 4A is a side view of a section of one embodiment of the linkage in a slack state.
FIG. 4B is a perspective view of the embodiment in FIG. 4A showing a portion of the linkage and gripping head with the linkage in the taut state.
Figure 4C:
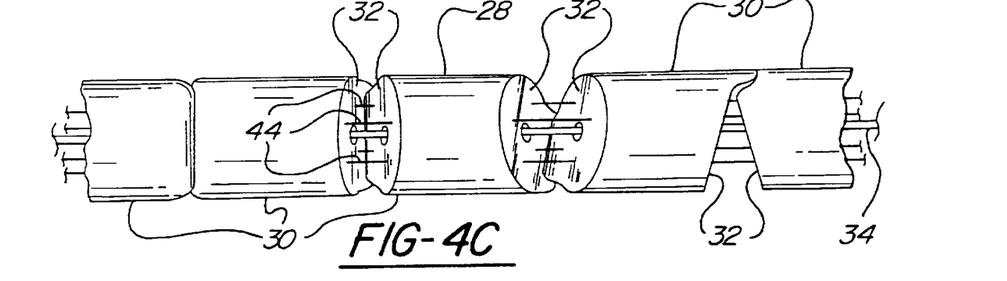
FIG. 4C is a plan view of the embodiment in FIG. 4A showing a portion of the linkage in a slack state.

As discussed above, the apparatus includes a linkage 28 having several elements 30. The elements 30 each have opposing alignment surfaces 32 that have predetermined orientations with respect to the draw line 34. The exact orientation of each alignment surface 32 in the linkage 28 is precisely determined to ensure proper functioning of the linkage 28. The linkage 28 functions properly when it directs the gripping head 24 to the proper location in the fundus, then retracts—with the alignment surfaces 32 engaging one another—to position the gripped portion of the fundus in front of the esophagus with the anvil surface 40 aligned precisely with the fastener applicator 20. The anvil surface 40 will thereafter remain approximately 10–15 millimeters from the face of the fastener applicator 20. As shown in FIGS. 4A and 4C, the alignment surfaces may have unusual non-planar or wavy shapes.

As noted, the apparatus includes some type of fastener applicator 20. In the preferred case the applicator 20 is a stapler of the type shown in FIG. 2D and discussed later in connection with the alternative embodiment. Appropriate staplers are well-known to persons of skill in the art, and several types of staplers will suffice. One example appears in the U.S. Pat. Nos. 5,676,674 and 5,571,116 to Bolanos et al. The teachings of these patents are incorporated herein by reference. One desirable feature of whatever stapler is used relates to the ability to select staple size during the procedure. Once size is determined, one should be able to feed a cartridge of desired staples into the proximal end of the apparatus and direct the cartridge through a staple conduit, or along a staple track, to the stapler at the proximal end where the staples will be fired.

Figure 5:
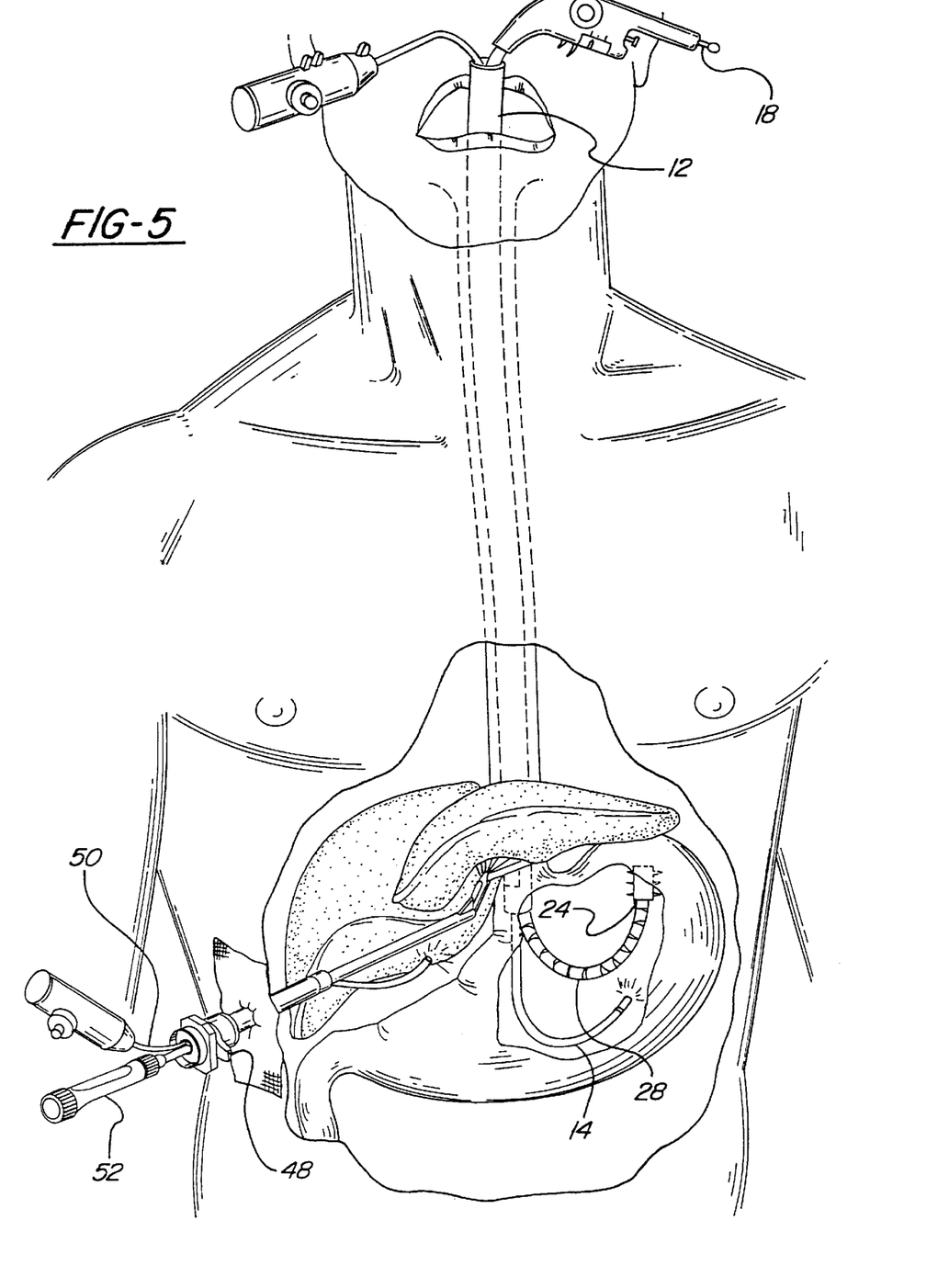
FIG. 5 is a front perspective view showing an optional use of a trocar and retractor to perform a portion of the novel method.

One might need a specialized trocar 48 in some circumstances. This is shown in FIG. 5. The specialized trocar 48 has a ten millimeter diameter with a five millimeter channel for a viewing laparoscope 50. The rest of the diameter provides clearance for a three-pronged retractor 52 that can be advanced under the liver edge and then flexed to lift the left lobe of the liver. The trocar 48 also has an air-insufflating channel. Using this trocar 48, the procedure can be done under direct videoscopic visualization.

Another embodiment of the apparatus is shown in FIGS. 6 through 14. This embodiment consists of a round sheath or conduit 112 comprising the following channels or conduits:

1. A channel 114 to allow the introduction of a visualizing scope 116 such as a pediatric gastroscope.

2. Another channel 118 (in FIG. 14) ends in a 1.5 to 2.5 cm. staple cartridge 120. These cartridges 120 can be replaced during the procedure. Available cartridges 120 will be of different lengths and the staples are also of varying depth of penetration. This will allow for the fashioning of wraps of varying lengths and the approximation of tissues of different thickness.

3. A third channel 122 supports the staple anvil assembly 124 including the anvil 126. This anvil 126 is carried on an extending arm 128 that can be manipulated outwardly and in different axes. At the periphery of the anvil 126, toothed prongs 130 can be extended to attach to the mucosa and gastric wall. These prongs 130 can be retracted or advanced by a prong control 132 from the proximal end. Once the mucosa is grasped, the anvil 126 first rotates in a counter-clockwise 90-degree arc. The purpose of this 90-degree counter-clockwise rotation is that it will allow the anterior wall of the stomach to fold over itself and not buckle up as the arm goes into the arc of opposition. Possible means for accomplishing this rotation have been discussed in connection with the first embodiment. The extending arm 128 is then locked and can only go into a circular arc that will oppose the stapler cartridge 120 and the anvil 126. The arc of this arm 128 will depend on links 134–144 that, when locked, will bring the anvil 126 and the cartridge 120 to ten millimeters of each other. Further fine adjustment will be done by screw mechanism 146 with an external color-coded marker 147. Three triggers 134, 148, 150 are placed on the instrument handle that will remain outside the mouth during use. All triggers are attached to, or otherwise associated with, cables or core elements. The first trigger 134 connects to trigger cable 133. Pulling the first trigger 134 advances the four to six prongs 130 located at the corners of the anvil 126. These prongs 130 are sharp and come out in a circular or rotary way, so that if the anvil 126 is placed directly against the mucosa, the prongs 130 will grip the stomach wall. The prongs 130 can also be released and retracted into their slots 152, allowing the release of the stomach wall if necessary. Pulling the second trigger 148 will rotate the anvil in the counter-clockwise 90-degree arc mentioned above. Pulling the third trigger 150 will carry out the circular arc that will oppose the anvil 126 and cartridge 120. This can be accomplished as set forth above in the discussion of the first embodiment, or with the use of the motor and tendon assemblies set forth below. Tightening the screw 146 that further approximates the anvil 126 and cartridge 120 will bring a marker 147 into view in a color-coded window 149 indicating what length of staple should be used. The staple cartridges 120 are similarly color-coded so that the appropriate cartridge is then selected based on the color that will correspond to the thickness of the tissues. The cartridge 120 can then be fired.

Figure 13A:
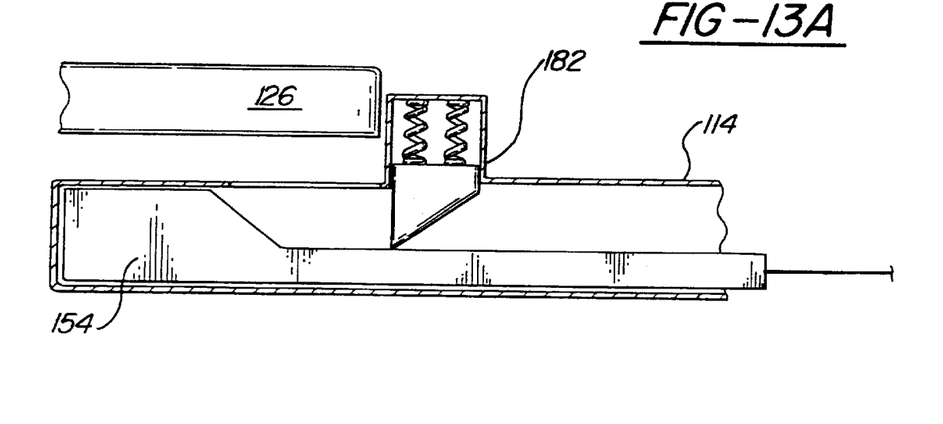
FIGS. 13A–C show an embodiment of the fastener applicator and the sequence of its operation in firing staples.
Figure 13B:
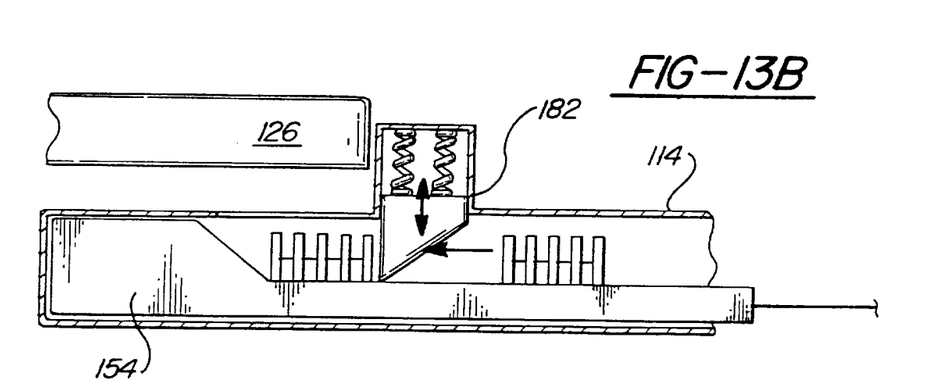
Figure 13C:
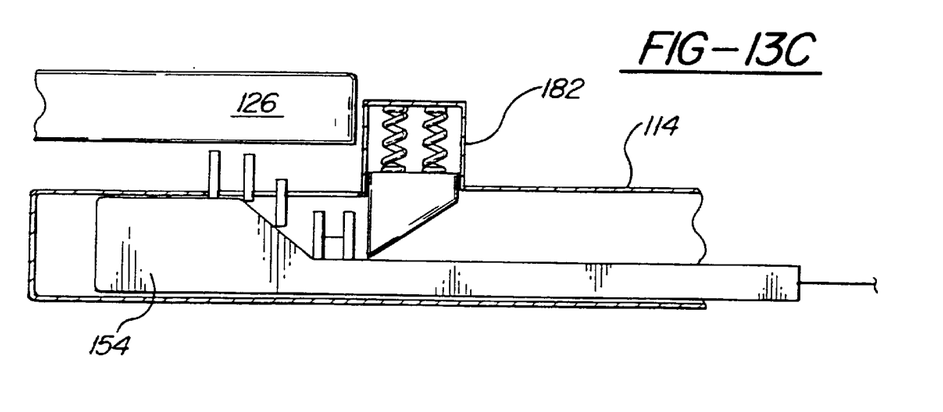

4. The cartridges 120 carry staples of 5, 7, or 9 millimeter length to accommodate different thickness of tissues. The cartridges come in 15 and 25 millimeter lengths if necessary. In the case of dysmotility the shorter cartridge is used, whereas if the motility is normal the longer cartridge is selected. The cartridge 120 carries 4 rows of staples that alternate in position along each row. Each staple is U-shaped in the unfired state. Pulling an elevated hammer under them forces them against the anvil 126. This is shown in FIGS. 13A–C. Slots in the anvil 126 shape the distal ends of the staples into two interlocking circles, thus stapling the tissues to each other. Other lengths of staples and cartridges may also be used or partial firings may allow the use of one length.

5. An optional specialized trocar 48 has a ten millimeter diameter with a five millimeter channel for a viewing laparoscope 50. The rest of the diameter accommodates a pronged retractor 52 that can be advanced under the liver edge and then flexed to lift the left lobe of the liver. The trocar 48 also has an air-insufflating channel. Using this trocar 48, the procedure can be done under direct videoscopic visualization. This situation is illustrated in FIG. 5, and has been previously discussed in connection with the first embodiment.

Figures 6, 7:
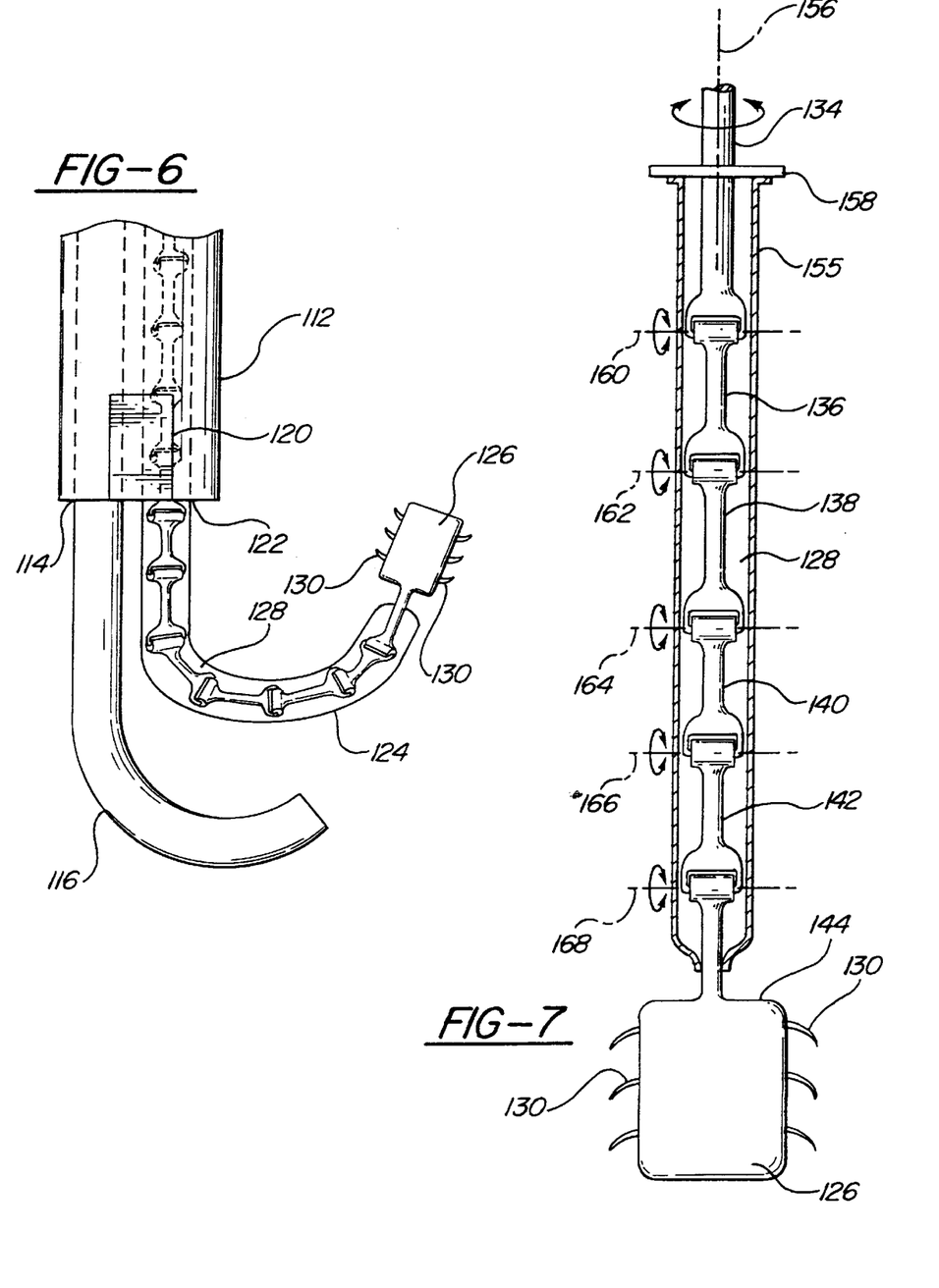
FIG. 6 is a front schematic view of an alternative embodiment of the apparatus shown in operation with the gripping head preparing to grip the fundus.
FIG. 7 is a front view of the alternative embodiment showing a portion of the linkage and the gripping head.
Figure 10:
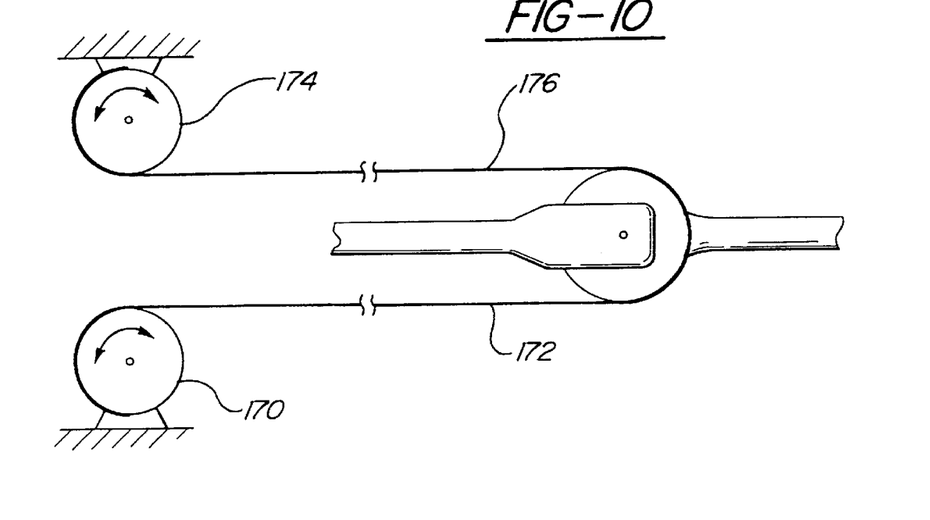
FIG. 10 is a schematic side view of a portion of the linkage and associated motor controls.

The multi-linked chain of links 134–144 functions like a robot arm to grasp the mucusa and move it into position for stapling. FIG. 7 illustrates the concept by means of a chain with six links in the housing 155. However, the final design may have fewer or more links, as required. The chain has a base link, as shown at 134. The link 134 rotates about the axis 156. Link 134 is attached to the housing 155 by means of a revolute or pin joint 158. Link 136 is attached to the link 134 by means of another revolute joint, the axis of which is represented by axis 160 in FIG. 7. Axis 160 is at right angles to axis 156. Link 138 is attached to link 136 by means of a revolute joint, with axis of rotation represented by axis 162 in FIG. 7, and so on. Axes 160–168 are parallel to each other and are at right angles to axis 156. The actuation of these various joints to effect the desired motion of the anvil 126 may be achieved by tendon-drives. These are TEFLON-coated steel cables that wind around the axes of the various joints. The cables are pulled by means of electric motors to effect joint rotation. This is an adaptation of the scheme used in the Stanford/JPL hand (Reference: Robot Hands and the Mechanics of Manipulation, by Matthew T. Mason and J. Kenneth Salisbury, MIT Press, 1985), the teachings of which are incorporated herein by reference. FIG. 10 shows how a representative joint is driven by means of a tendon drive. Motor 170 rotates the joint in the clockwise direction by pulling on tendon 172. Motor 174 rotates simultaneously to accommodate this motion by freeing-up some of tendon 176. In similar fashion, motor 174 rotates the joint in the counter-clockwise direction by pulling on tendon 176. Motor 170, in turn, accommodates this motion. By pretensioning these tendons one may ensure that there will be no slack in the system. Of course, such an arrangement could lead to a large number of motors. However, the use of the tendons enables the operator to locate the motors remote from the site of the surgical procedure. Therefore, the mass, size, and number of motors is not a limitation on the design. The motors may be mounted on the apparatus (which one might call a "fundoplicator"), sufficiently upstream of the patient, that their mass may be supported by a ceiling-mounted fixture. This arrangement is generally shown at 178 in FIG. 14. In theory, one requires n+1 motors and tendons to control n joints in series. The present design uses 2 n motors to control n joints. Alternative designs incorporating fewer motors are clearly possible.

Figure 11:
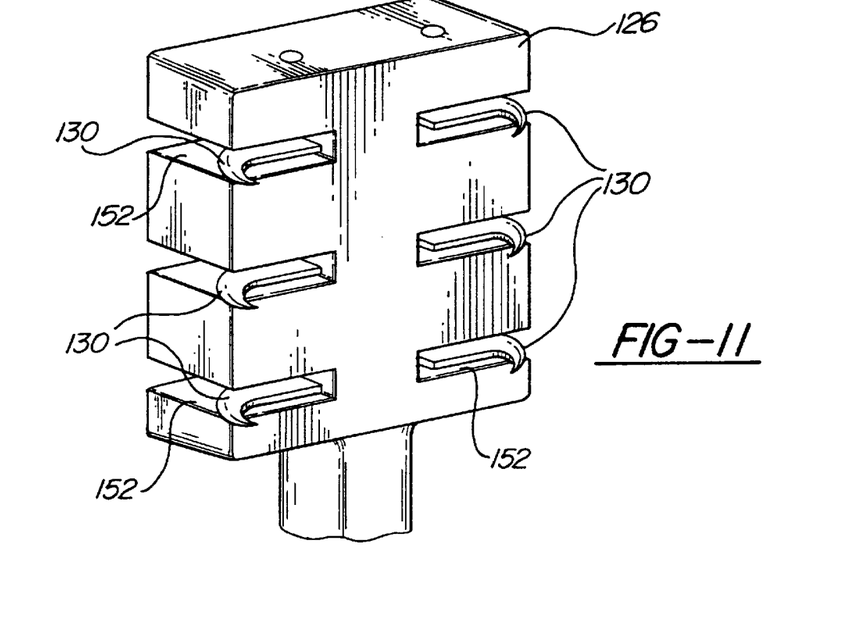
FIG. 11 is a perspective view of an alternative embodiment of the gripping head.
Figure 12A:
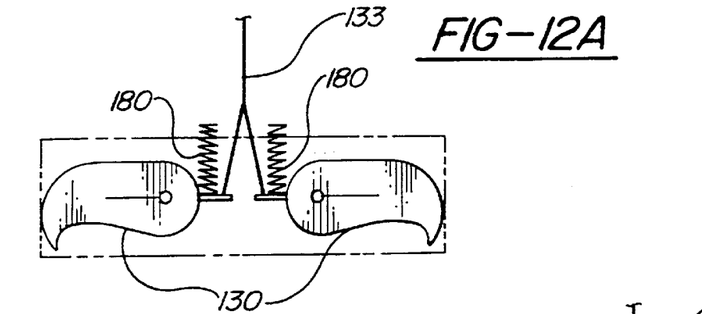
FIGS. 12A and 12B are schematic side sectional views of the gripping head of FIG. 11 showing an assembly for pivoting the gripping fingers.
Figure 12B:
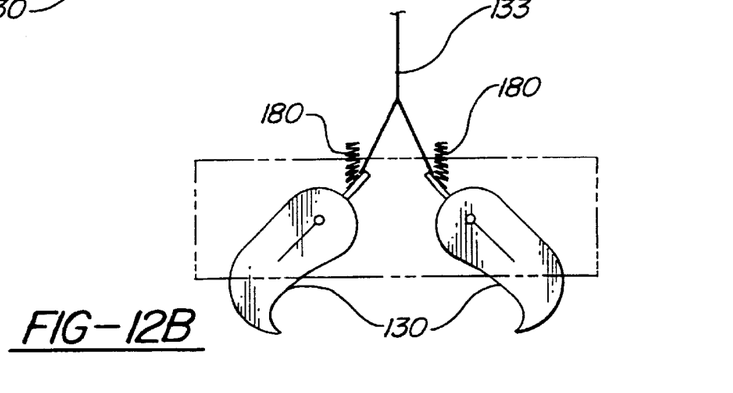

FIGS. 6–8 and FIG. 14 show the anvil 126 and its gripping mechanism, at the end of the multi-link chain of links. This device may be actuated by means of tendons pulled by electric motors, or simply manually. FIGS. 11 and 12A show the device with the claws or prongs 152 retracted inwardly. The claws 152 are held in this retracted position by means of appropriately located compression springs 180. FIG. 12B shows the device with the claws extended outwardly for effective grasping. This position is achieved by having a manual or motor-driven force pull on the tendon 133, overcoming the spring force and rotating the claws 152 about their pivots.

Figure 8A:
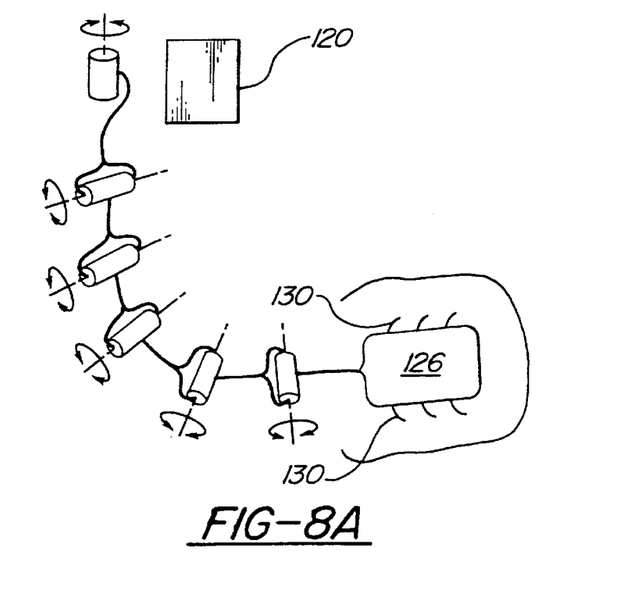
FIG. 8A is a front schematic view of the alternative embodiment showing the gripping head beginning to grip the stomach wall.
Figure 8B:
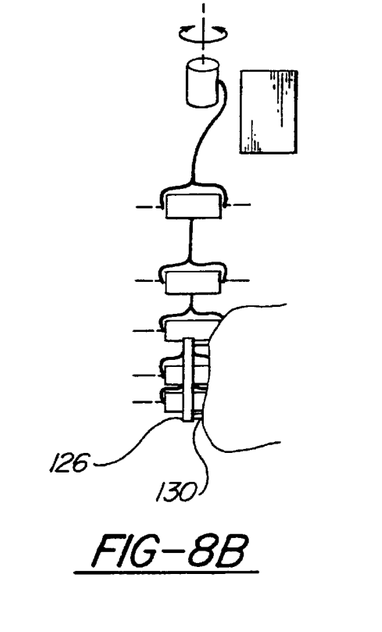
FIG. 8B is similar to FIG. 8A showing the gripping head gripping the stomach and after the gripping head has rotated ninety degrees about the axis of the linkage.
Figure 8C:
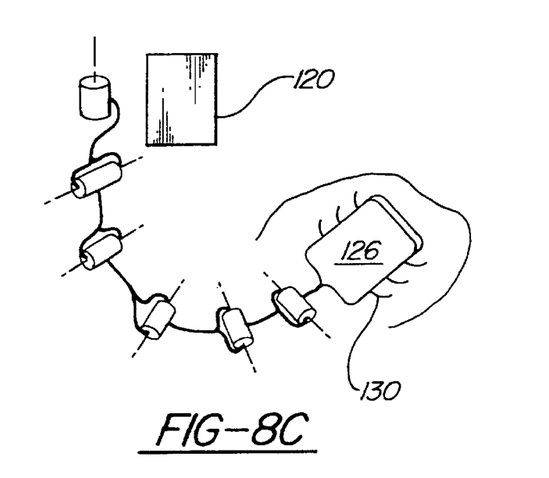
FIG. 8C is similar to FIG. 8A showing the linkage in an intermediate position.
Figure 8D:
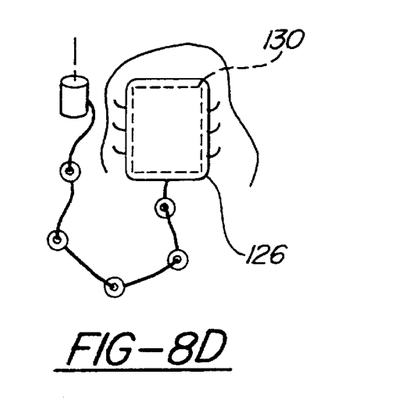
FIG. 8D is similar to FIG. 8C showing the linkage in its final position with the gripping head and gripped portion of the stomach positioned in front of the fastener applicator.

The full travel of the anvil 126 is shown in FIGS. 8A–8D. The anvil 126 moves with the assistance of the linkage from its initial position (FIG. 8A) where it first grips the anterior part of the fundus, to an intermediate position where the anvil 126 rotates ninety degrees about the axis of the linkage (FIG. 8B), to its final position adjacent the stapler cartridge (FIGS. 8C and D).

Figure 9:
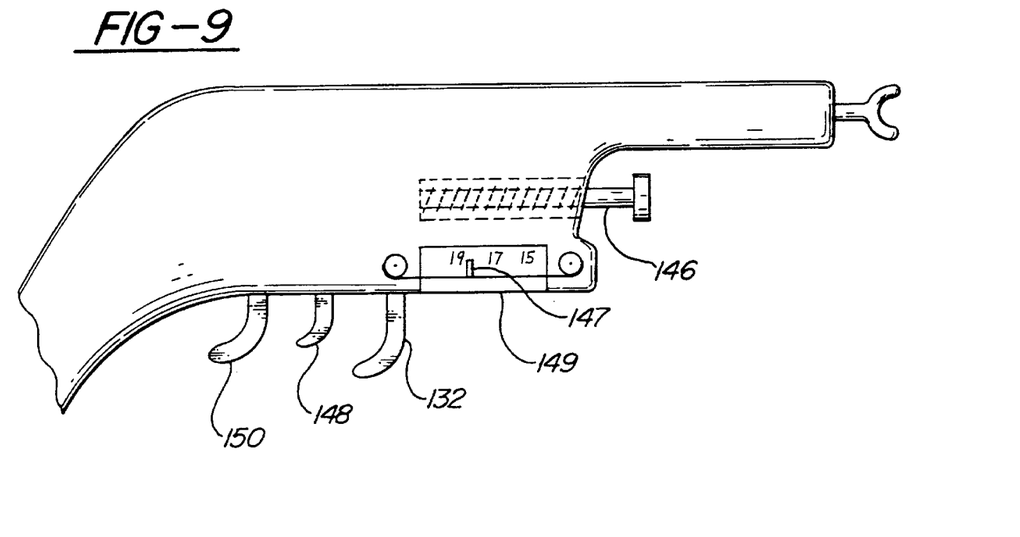
FIG. 9 is a side view of the handle at the proximal end of an embodiment of the apparatus.
Figure 14:
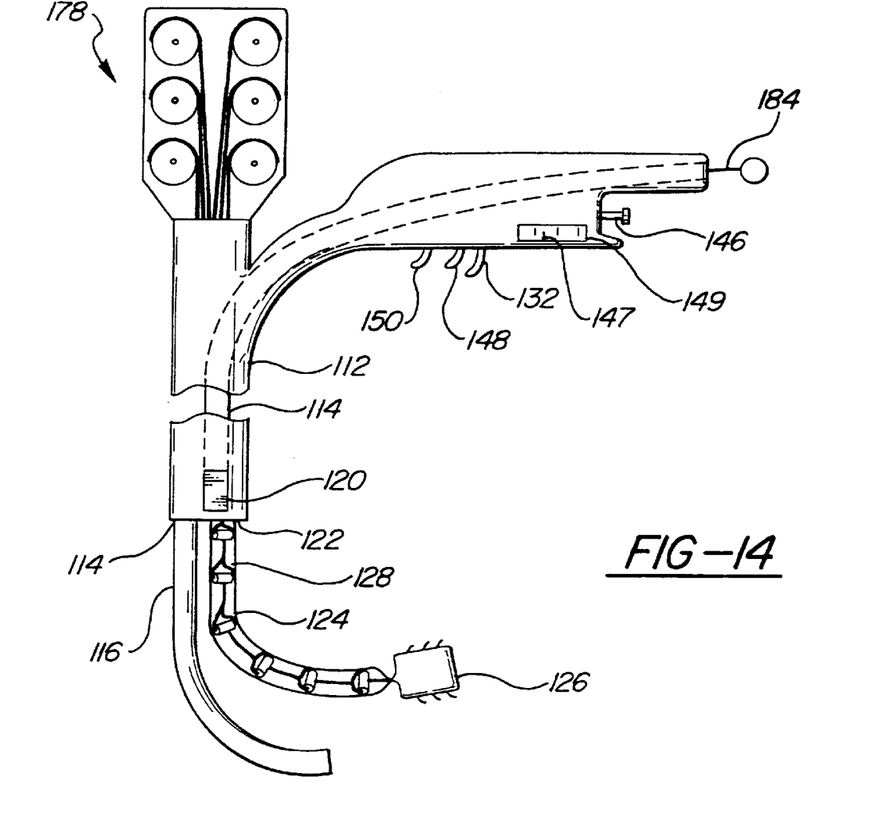
FIG. 14 is a side view of an alternative embodiment of the apparatus.
Figure 15:
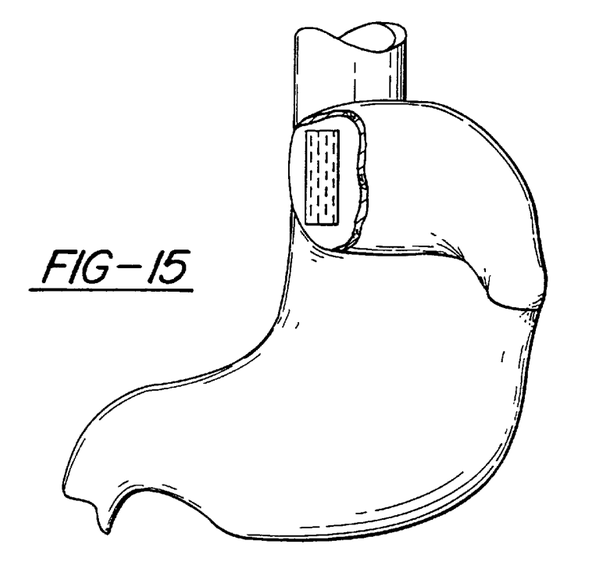
FIG. 15 is a front view of the result of a fundoplication according to the present method showing the stomach stapled to the esophagus.

Fine motion of the end-effector or anvil 126 towards the stapling cartridge 120 may be achieved by means of the screw 146 shown in FIGS. 9 and 14. This screw 146 is linked to a potentiometer, which controls the motors pulling on the various tendons actuating the joints of the multi-linked chain. In addition, the motor rotations are used to calculate the positions of the anvil 126 relative to the stapling cartridge 120 and this is indicated by means of the marker 147 moving into appropriate color zones as mentioned earlier in connection with the description of FIGS. 10 and 14.

The actual mechanism for firing the staples in the stapling cartridge is shown in FIGS. 13A–C. The mechanism is comprised of a sliding block or hammer 154 and a detent mechanism 182. This block 154 is initially held in the position shown in FIG. 13A. A set of staples is inserted into the mechanism and pushed past the detent mechanism 182 (see FIG. 13B). The detent mechanism 182 slides upwardly as the staples are pushed past it and then snaps down again to hold the staples in place and prevent them from moving back up the conduit 114. To fire the staples, the sliding block 154 is pulled to the right as shown in FIG. 13C. This motion of the sliding block 154 is achieved by pulling on the stapling pin 184 located in the handle of the apparatus (see FIGS. 9 and 14). The inclined angle of attack—or cam surface—of the sliding block 18 ensures that the staples are sequentially pushed upwardly, toward the anvil 126, which turns the staple ends downward and inward to complete the stapling operation. The sliding block 154 may be moved to the extent desired, to fire as many or all staples as required.

FIG. 14 shows the entire apparatus (called a "fundoplicator"), including the handle (with all of its triggers and gages), the gastroscope 116, the anvil assembly 124 with the prongs 130, the stapling cartridge 120, as well as the bank of electric motors 178 to drive the tendons of the mechanism.

METHOD

This description also sets forth a novel method for performing a non-invasive fundoplication. This method and its variants may be performed with the previously discussed apparatuses, or with some different apparatus. The method includes the basic steps of: inserting a device through the mouth and esophagus of a patient to a predetermined location near the gastro-esophageal junction; viewing portions of the stomach and esophagus with the device; engaging a portion of the inside anterior wall of the stomach with the device at a location between the greater curvature and the gastro-esophageal junction; moving the portion of the wall with the device to a location adjacent the esophagus; and securing it to the esophagus with the device at a location remote from the fundus. The overall process is shown in FIGS. 2A–D and FIGS. 8A–8D.

This method is somewhat related to the aforementioned Dor technique for fundoplication in that it involves gripping a certain portion of the fundus, pulling the fundus across the front face of the esophagus, and attaching the fundus to the esophagus. The present method differs, however, in some key respects, because it involves a non-invasive way to perform the basic procedure, and because it attaches the fundus more to the distant side of the esophagus rather than to the front.

Figure 2A:
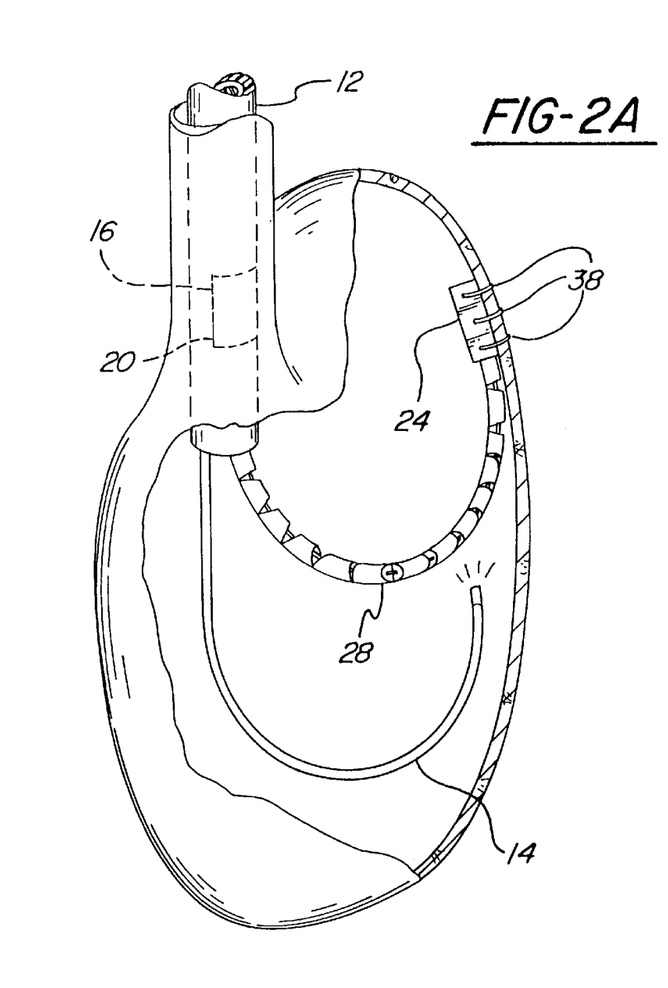
FIG. 2A is an enlarged side view of the arrangement shown in FIG. 1.

The step of engaging includes the step of gripping with a gripping device. Conceivably the step of engaging could be performed with suction, but the presently preferred technique involves gripping with a gripper, perhaps of the type shown at 22 or 126 the Figures. The step is shown in FIGS. 1, 2A, and 8A.

The step of gripping could include a variety of pinching or grasping techniques. The presently preferred method includes the step of extending a plurality of gripping fingers 38 from the device 24 in the manner shown in the Figures to make fine penetrations in the mucosa.

According to the inventive method, a device grips a certain part of the stomach and attaches it to a certain part of the esophagus. A device grips the anterior part of the fundus approximately half-way between the esophagus and the greater curvature, as shown in the Figures, especially FIGS. 1, 5, and 8. The anterior portion of the fundus is then secured to the side of the esophagus remote from the fundus. In the typical patient, this is the left side of the esophagus when viewed from the front of the patient. In other words, this is the side of the esophagus extending proximally or cephalad from the lesser curvature of the stomach. The attachment occurs along a length of the esophagus from the gastro-esophageal junction upwardly approximately a few centimeters.

Figure 2B:
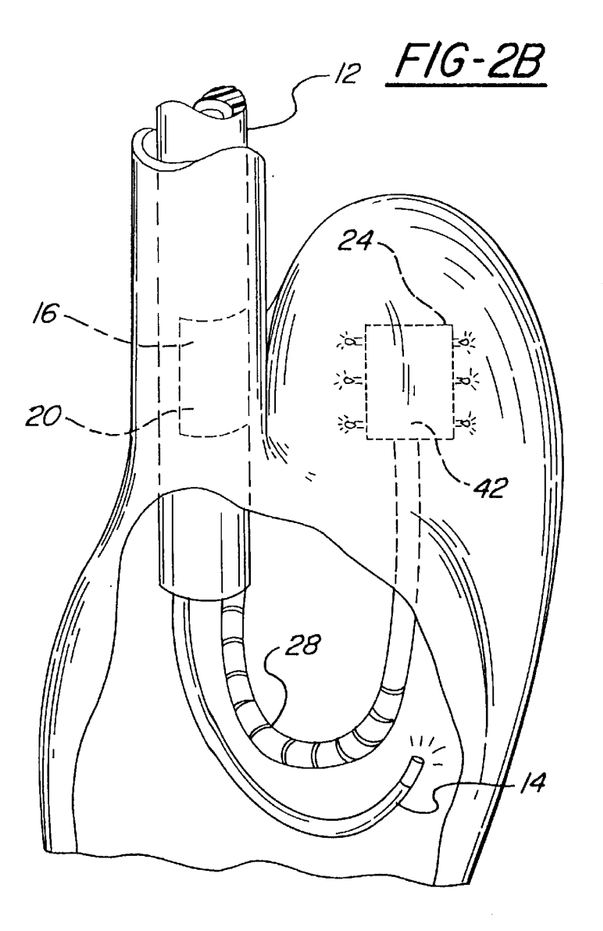
FIG. 2B is an enlarged side view of the arrangement shown in FIG. 2A with the gripping head and the fundus rotated ninety degrees from the position in 2A.
Figure 2C:
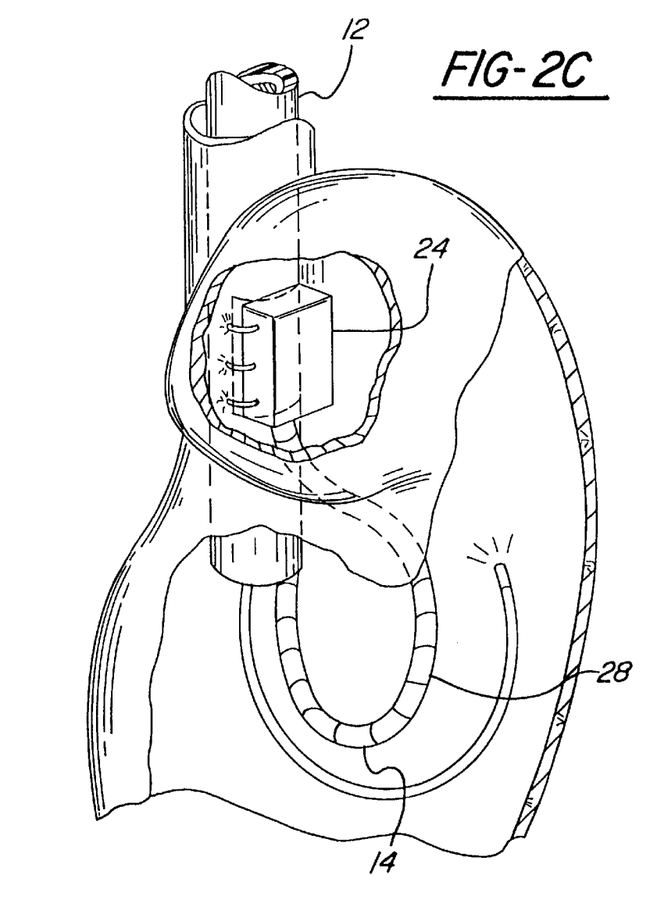
FIG. 2C is an enlarged side view of the arrangement shown in FIG. 2A with the gripping head and the fundus moved into position on the side of the esophagus in preparation for fastening.
Figure 2D:
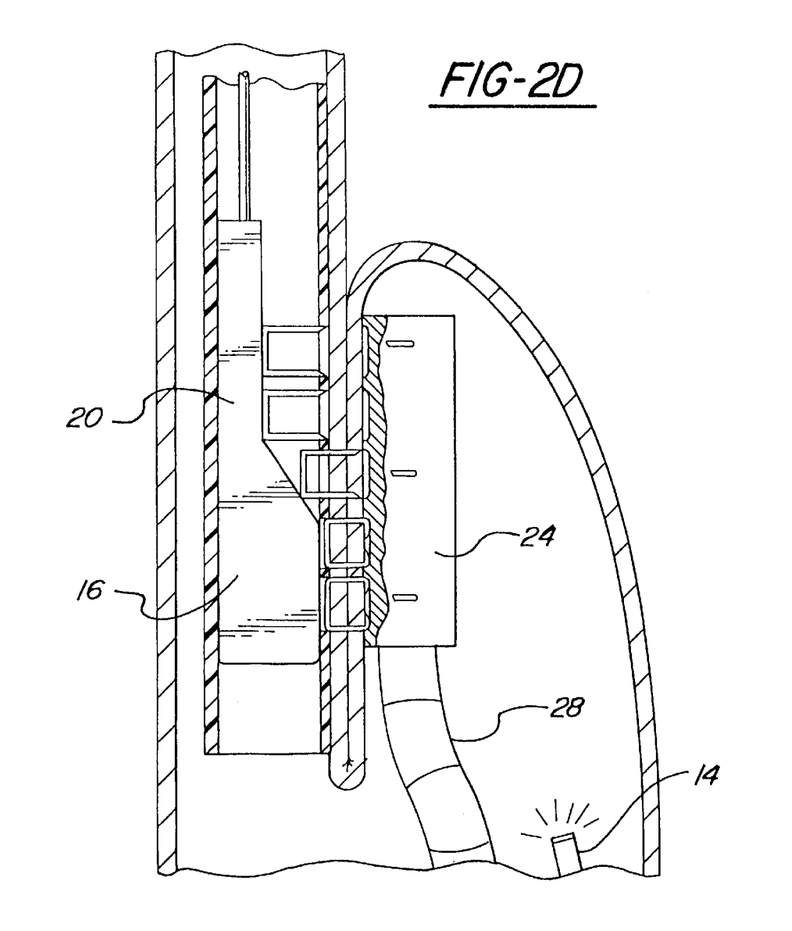
FIG. 2D is a different enlarged side view of the arrangement shown in FIG. 2C showing the stapler and anvil fastening the fundus and the esophagus.

Next, one performs the step of rotating the portion of the stomach ninety degrees after the step of engaging the portion. This may be performed, for example, with either of the embodiments shown above wherein the gripping head 24 rotates ninety degrees about the axis of the linkage 28. The point of this step is to fold over the anterior wall of the stomach so it will not buckle up as it is being moved into the fastening position adjacent the esophagus. This rotating step is shown in FIGS. 2B and 8B.

The method also includes the step of positioning a fastener applicator in a predetermined location between the gastro-esophageal junction and the proximal end of the esophagus. This prepares the applicator to deliver the fasteners in the correct location. The step may be performed at various times prior to when the stomach is moved in front of the esophagus. It is presently contemplated that the applicator—e.g. the stapler 20—is positioned at the beginning of the procedure before the stomach portion is gripped or moved. This is shown in several of the Figures, including FIGS. 1, 2A–D, and 8A–D.

The step of moving the gripped portion of the stomach may be accomplished with the apparatuses set forth above or with some other apparatus. The step involves drawing the portion of the fundus to the preferred location on the side of the esophagus. In the embodiments shown in the Figures, the portion of the fundus and the esophagus are aligned between the face of the stapler 20 and the face of the anvil 40, which are aligned essentially parallel to one another and spaced apart from one another a few—maybe 10 to 15—millimeters.

The securing step may be executed in a number of ways. Preferably, it is accomplished with a stapler such as the one indicated at 20. In the disclosed embodiments, there is some means—e.g. 147, 149—for gauging the distance between the stapler and the anvil surface. One can select the staple size based on the distance.

The method might involve additional steps relating to the use of a trocar 48, a viewing device 50, and a device 52 to move the liver. In the preferred method, these steps are not necessary; but they might be used if desired under certain circumstances. The additional steps are: inserting a trocar adjacent the liver; inserting a viewing device through the trocar; inserting a moving device through the trocar; and manipulating the liver with the moving device. This is shown in FIG. 5. The trocar 48 is an air-insufflating trocar with a diameter of approximately ten millimeters. The moving device is a retractor such as 52. The viewing device 50 is a laparoscope.

At the end of the entire procedure, the gripping fingers (e.g. 30) release the fundus and the entire apparatus may be removed from the patient.

The invention has been described in an illustrative manner, and it is to be understood that the terminology which has been used is intended to be in the nature of words of description rather than of limitation.

Obviously, many modifications and variations of the present invention are possible in light of the above teachings. Therefore, it is to be understood that within the scope of the appended claims the invention may be practiced otherwise than as specifically described. Moreover, the reference numerals are merely for convenience and are not intended to be in any way limiting.

I claim:

1. A method for non-invasive treatment of internal body tissue comprising the steps of:

inserting a device through the mouth and esophagus of a patient to a predetermined location near the gastro-esophageal junction;

viewing portions of the stomach and esophagus with the device;

engaging a portion of the inside wall of the stomach remote from the gastro-esophageal junction with the device;

moving the portion of the inside wall with the device to a location adjacent the esophagus; and securing the portion to the esophagus with the device;

wherein the step of engaging includes the step of gripping with a gripping device; and wherein the step of gripping includes the step of extending a plurality of gripping fingers from the device.

2. The method of claim 1 wherein the anterior portion of the fundus remote from the esophagus is secured to a portion of the esophagus above the gastro-esophageal junction.

3. The method of claim 2 wherein the anterior portion of the fundus is secured to the side of the esophagus remote from the fundus.

4. The method of claim 3 wherein the device grips the fundus approximately half-way between the esophagus and the greater curvature of the stomach.

5. The method of claim 1 wherein the securing is accomplished with a stapler.

6. The method of claim 1 further including the step of rotating the portion ninety degrees after the step of engaging the portion.

7. The method of claim 1 further including the step of positioning a fastener applicator in a predetermined location between the gastro-esophageal junction and the proximal end of the esophagus.

8. The method of claim 1 further including the steps of: inserting a trocar adjacent the liver; inserting a viewing device through the trocar; inserting a moving device through the trocar; and manipulating the liver with the moving device.

9. A method for performing a non-invasive fundoplication including the steps of:

inserting a device through the mouth and esophagus of a patient to a predetermined location near the gastroesophageal junction;

viewing portions of the stomach and esophagus with the device;

engaging a portion of the inside anterior wall of the stomach with the device at a location between the greater curvature of the stomach and the gastroesophageal junction;

moving the portion of the inside wall with the device to a location adjacent the esophagus; and securing the portion to the esophagus with the device at a location remote from the fundus;

wherein the step of engaging includes the step of gripping with a gripping device; and wherein the step of gripping includes the step of extending a plurality of gripping fingers from the device.

10. An apparatus for treating internal body parts comprising:

a flexible elongated conduit having a proximal end and a spaced apart distal end;

a viewing device disposed through the conduit;

a fastening device disposed through the conduit, the fastening device having an actuator at the proximal end and a fastener applicator at the distal end; and an elongated gripper mechanism extending through the conduit, the gripper mechanism including a gripping head disposed at a distal end of the gripper mechanism capable of moving between a starting configuration and a gripping configuration in which the gripping head grips desired body tissue, a manipulable control at a proximal end of the gripper for controlling the position and configuration of the gripping head, and an elongated linkage extending along an axis to interconnect the control and the gripping head, the linkage being adapted to move the gripping head in response to manipulation of the control; wherein the gripping head includes a block having a gripping face and a plurality of gripping fingers pivotally attached to the block for movement between a retracted position behind the gripping face and an extended position where the gripping fingers extend beyond the gripping face to grip desired tissue.

11. The apparatus of claim 10 wherein the linkage includes a plurality of elements disposed in series along the axis, each of the elements including at least two alignment surfaces extending across the axis and having a predetermined orientation with respect to the axis, the linkage further including an elongated draw line extending between the control and the linkage and through the elements, the draw line being moveable between a slack state and a taut state wherein the elements abut at the alignment surfaces so that the linkage assumes a predetermined configuration with the gripping head surface disposed adjacent the fastener applicator.

12. The apparatus of claim 10 wherein the gripping face includes an anvil surface defining a plurality of shallow cavities for shaping fasteners.

13. The apparatus of claim 10 further including a plurality of positioning cables extending along the linkage for controlling movement of the gripping head.

14. The apparatus of claim 10 further including a rotating assembly associated with the gripping head for rotating the gripping head about the axis.

15. The apparatus of claim 14 wherein the rotating assembly includes a motion transmitting rotation core element extending along the linkage between the control and the gripping head.

16. An apparatus for treating internal body parts comprising:

A flexible elongated conduit having a proximal end and a spaced apart distal end;

a viewing device disposed through the conduit;

a staple delivery assembly disposed through the conduit, the staple delivery assembly having an actuator at the proximal end, a staple applicator at the distal end, and a staple conduit interconnecting the actuator and the applicator; and an elongated gripper mechanism extending through the conduit, the gripper mechanism including a gripping head disposed at a distal end of the gripper mechanism capable of moving between a starting configuration and a gripping configuration in which the gripping head grips desired body tissue with a plurality of gripping fingers, a manipulable control at a proximal end of the gripper for controlling the position and configuration of the gripping head, an elongated linkage extending along an axis to interconnect the control and the gripping head, the linkage being adapted to move the gripping head in response to manipulation of the control, the linkage defining an axis extending from the control to the gripping head, and the linkage including a plurality of links disposed in series along the axis, and a plurality of elongated core elements extending along the axis for controlling the gripping head; wherein the gripping head includes a block having a gripping face and a plurality of gripping fingers pivotally attached to the block for movement between a retracted position behind the gripping face and an extended position where the gripping fingers extend beyond the gripping face to grip desired tissue.

* * * * *